US011351213B2

(12) United States Patent
Di Maio

(10) Patent No.: US 11,351,213 B2
(45) Date of Patent: Jun. 7, 2022

(54) COMPOSITION FOR THE PREVENTION AND/OR TREATMENT OF RESPIRATORY TRACT DISORDERS

(71) Applicant: NEILOS S.R.L., Piano di Sorrento (IT)

(72) Inventor: Umberto Di Maio, Piano di Sorrento (IT)

(73) Assignee: NEILOS S.R.L., Piano di Sorrento (IT)

(*) Notice: Subject to any disclaimer, the term of this patent is extended or adjusted under 35 U.S.C. 154(b) by 33 days.

(21) Appl. No.: 16/649,583

(22) PCT Filed: Sep. 28, 2018

(86) PCT No.: PCT/IB2018/057555
§ 371 (c)(1),
(2) Date: Mar. 20, 2020

(87) PCT Pub. No.: WO2019/064255
PCT Pub. Date: Apr. 4, 2019

(65) Prior Publication Data
US 2020/0254043 A1 Aug. 13, 2020

(30) Foreign Application Priority Data

Sep. 28, 2017 (IT) .................. 102017000109080

(51) Int. Cl.
*A61K 36/00* (2006.01)
*A61K 36/19* (2006.01)
*A61P 11/10* (2006.01)
*A61P 11/14* (2006.01)
*A61K 9/00* (2006.01)
*A61K 31/198* (2006.01)
*A61K 36/185* (2006.01)

(52) U.S. Cl.
CPC ............ *A61K 36/19* (2013.01); *A61K 9/0043* (2013.01); *A61K 9/0053* (2013.01); *A61K 9/0073* (2013.01); *A61K 31/198* (2013.01); *A61K 36/185* (2013.01); *A61P 11/10* (2018.01); *A61P 11/14* (2018.01)

(58) Field of Classification Search
CPC ........... A61P 31/16; A61P 11/00; A61P 11/14; A61P 11/10
See application file for complete search history.

(56) References Cited

U.S. PATENT DOCUMENTS

2004/0265381 A1* 12/2004 Shanghvi ............... A61P 11/06
424/468
2015/0273009 A1* 10/2015 Cifter ..................... A61K 36/25
424/756
2016/0113876 A1* 4/2016 De Lazzari .......... A61K 9/2009
514/562

FOREIGN PATENT DOCUMENTS

DE 4103360 A1 8/1992

OTHER PUBLICATIONS

Agbabiaka et al., "Pelargonium sidoides for acute bronchitis: A systematic review and meta-analysis", Phytomedicine, 2008, 15: 378-385.
Herrmann et al., "Adhatoda vasica—Justicia adhatoda: Rediscovering an old herbal plant", Zeitschrift Fur Phytotherapie 2006 DE, 2006, 27(6): 306-310.
Terlizzi et al., "The combination of N-Acetyl-L-Cysteine, Pelargonium sidoides and Justicia adhatoda (NAXX) exerts bacteriostatic activity against *S. aureus* and *E. coli*", Natural Product Research, May 2020, 35(23): 5360-5363.

* cited by examiner

*Primary Examiner* — Qiumen Mi
(74) *Attorney, Agent, or Firm* — James S. Keddie; Bozicevic, Field & Francis LLP

(57) ABSTRACT

The present invention relates to a composition comprising or, alternatively, consisting of an effective amount of a mixture which comprises at least, or consists of: a) an extract of *Pelargonium sidoides*; b) an extract of *Adhatoda vasica*; and c) N-acetyl cysteine for use in a method for the preventive or therapeutic treatment of at least one respiratory tract disorder in a subject, wherein said treatment method comprises the administration of said composition to the subject.

9 Claims, No Drawings

COMPOSITION FOR THE PREVENTION AND/OR TREATMENT OF RESPIRATORY TRACT DISORDERS

CROSS-REFERENCE TO RELATED APPLICATIONS

This application is a § 371 national phase of International Application No. PCT/IB2018/057555, filed on Sep. 28, 2018, which claims the benefit of Italian Application No. 102017000109080, filed on Sep. 28, 2017, which applications are incorporated by reference herein.

The present invention relates to a composition for use in a method for treating respiratory tract disorders or diseases, wherein said composition, in any form of pharmaceutically acceptable administration thereof, comprises a mixture comprising or, alternatively, consisting of an extract of *Pelargonium sidoides*, an extract of *Adhatoda vasica* and N-acetyl cysteine.

The respiratory system consists of different anatomical structures, which serve to ensure its correct functioning.

It has the function, in fact, of exchanging gases, oxygen and carbon dioxide, between tissues and the outside environment, a function that is fundamental for all of the body's cellular processes and thus for its life.

Anatomically, two macro areas can be distinguished, the upper and lower airways. The former consist of the nose, pharynx and associated structures, whilst the latter consist of the larynx, trachea, bronchi and lungs, whose actual respiratory surface consists of alveoli. This complex system of organs serves to prepare air for its entry into the lungs by filtering out any particulate matter and heating and humidifying it. Particles larger than 10-15 microns can be blocked at the level of the nasal cavities thanks to the hairs and the presence of mucus, which traps these particles, as well as precipitation due to turbulence, mediated by the turbinates, which divert the direction of air. Mucus is layered on top of the periciliary liquid, in which the vibratile cilia of epithelial cells are immersed. Particles of about 10 microns reach the trachea, are trapped in the mucus and then eliminated by ciliary movement. Particles of 2-5 microns settle in the terminal bronchioles due to gravitational precipitation, while those smaller than 2 microns are removed by alveolar macrophages and taken away by the lymphatic system of the lungs.

The entire respiratory tract consists of epithelial cells, which differ in type and function along the tracheobronchial tree. Ciliated columnar cells characterise the airways from the trachea to the terminal bronchioles. Protruding from their apical surface are the cilia, which have the task of moving with a cleaning effect on mucus and any inhaled particles.

Muciferous goblet cells have the function of secreting mucus, useful for maintaining the correct moisture of the epithelium and trapping particulate matter. They are present in the broadest sections of the airways, under the small bronchi, but have not been found in bronchioles.

All respiratory system components can be exposed to a series of diseases with varying etiologies, often sustained by different pathogenic microorganisms which, on becoming preponderant in the microenvironment and over the flora normally present, cause the disease and consequently lead to a reduced functionality.

Upper Respiratory Tract Pathologies
Rhinitis

Rhinitis is an inflammatory process affecting the mucosa of the nasal cavities and is distinguished between acute and chronic forms. Acute rhinitis is generally sustained by viruses, including Rhinovirus, Coronavirus, influenza and parainfluenza virus, RSV, Coxsackie virus, ECHO virus and adenovirus. Contagion occurs as a result of direct contact with an ill subject, who, at the peak of contagiousness (generally the first days), will have 500-1000 virions per ml of secretion, which he or she emitted through coughs and sneezes. It is possible for there to be bacterial superinfections, which lead to complications such as otitis and sinusitis. The common cold caused by Rhinovirus gives rise to acute symptoms in the first 3-4 days, whilst coughing and other symptoms persist for 7-10 days. There is an excess of mucus secretions that are fluid and transparent and become purulent and foul smelling in the event of bacterial superinfection.

The chronic form is generally secondary to sinusitis, nasal septum deviations and hypertrophic adenoids. Allergic rhinitis is of the acute type and is due to a subject's exposure to substances that provoke an IgE-mediated reaction, characterised by an excessive production of fluids, intranasal itching, sneezing and obstruction. IgE binds to mastocytes, which release large amounts of histamine, responsible for all pathological manifestations.

Recent studies have shown that allergic rhinitis and asthma are concurrent and to be considered as two manifestations of the entire respiratory tract, that is, rhinitis does not regard solely the upper part of the respiratory tract and asthma does not regard solely the lower part of the respiratory tract. In fact, it appears that between 20% and 50% of patients with allergic rhinitis also have asthma and from 30% to 90% of patients with asthma have concomitant rhinitis. Therefore, allergic rhinitis could be a predisposing factor for the development of allergic asthma and, more specifically, the sensitisation to aeroallergens (pollen or animal hair) would seem to be an important risk factor in the association of asthma and rhinitis.

Sinusitis

Sinusitis is an inflammation of the mucosa lining the paranasal sinuses, bone cavities that are situated in the facial skeleton and are in communication with the nasal fossae, and may thus become infected due to the same causes responsible for rhinitis. Sinusitis can be distinguished into: acute viral or acute bacterial (up to 4 weeks), chronic (over 12 weeks) and acute recurrent (at least 4 episodes a year with resolution).

When sinusitis involves the nasal cavity one speaks of rhinosinusitis. A healthy sinus is generally sterile, characterised by an appropriate drainage of mucus and a free passage of air. Ciliary abnormalities or immobility determine an inhibition of drainage resulting in sinusitis. Factors predisposing to this pathology are an immunocompromised state, nasal septum deviation, nasal polyps, tumours, traumas and fractures, cocaine abuse and the presence of foreign bodies.

An acute viral form of sinusitis can be susceptible to bacterial superinfection. The bacteria commonly responsible for these infections are *Streptococcus pneumoniae*, nontypeable *Haemophilus influenzae* and *Moraxella catarrhalis*. *Pseudomonas aeruginosa* is more frequently present in sinusitis caused by HIV infections and cystic fibrosis. Some genera of fungi such as *Candida, Aspergillus, Blastomyces, Coccidioides, Rizophus, Histoplasthma* and *Cryptococcus* can cause sinusitis in immunocompromised patients.

The signs and symptoms of acute rhinosinusitis consist in: mucopurulent discharges from the nose, nasal obstruction, congestion, facial pain, pressure on the sinuses involved, hyposmia, anosmia, fever, sensation of pressure or a "plug"

in the ears and toothache. In the first 3-5 days, a viral form cannot be distinguished from a bacterial one, so the use of antibiotics is not advisable.

If the pathology persists for over 10 days, it will very probably be sustained by bacteria and antibiotic treatment is indicated. Chronic forms have a slower onset, longer duration and greater frequency. The symptoms are similar to those of the acute form with, in addition, bad breath, laryngitis, bronchitis and a worsening of asthma.

Sinusitis often resolves on its own and treatment is prevalently symptomatic. In particular, decongestant treatment serves to reduce oedema, improve the drainage of excess mucus and maintain the patency of the sinus ostia. A good result can be obtained in the treatment of the acute bacterial, acute recurrent and chronic forms, as well as in prevention, by local application of a hypertonic saline solution.

The choice of antibiotics must take into account the production of beta lactamase and presence of drug-resistant pneumococci.

Pharyngitis (Pharyngotonsillitis)

It is an inflammatory process of the pharynx, hypo pharynx, uvula and tonsils, which is generally transmitted by direct contact with respiratory secretions. It is more frequent in paediatric age (5-15 years) and although it is often self-limiting, the swelling of the parts involved can cause a reduced patency of the airways or in any case preclude the ingestion of adequate amounts of liquids, with consequent dehydration.

The infection can be sustained by viruses (such as Epstein-Barr) and bacteria; in particular, group A beta-haemolytic *Streptococcus pyogenes* is the most frequent in paediatric forms, but *Micoplasthma pneumoniae* and *Clamidia pneumoniae* as well are found in adults and children. The forms transmitted through sexual contact and sustained by *Neisseria gonorrhoeae* and *Corynebacterium diphtheriae* (form reduced by use of a vaccine) should also be considered.

Epiglottitis

It is an inflammation of the epiglottis, caused by a viral or bacterial infection, which determines a swelling of the organ with a possible obstruction of the airways.

Epiglottitis is mainly caused by *H. influenzae* type b, but also by streptococci, staphylococci or a thermal trauma. It manifests itself with ear pain (in adults) and dysphonia, whilst fever is absent in up to 50% of cases and can develop at a late stage. The treatment is antibiotic when bacteria are the cause of the disease, whereas intubation may be required in the case of a severe obstruction of the airways.

Laryngitis

It is an inflammation of the larynx that manifests itself with aphonia and hoarseness, mainly caused by viruses, but also by bacteria (including streptococci and *C. diphtheriae*) in up to 10% of cases. Non-infectious causes can be tumours, thermal or caustic traumas or GERD (gastroesophageal reflux disease). Laryngitis manifests symptoms lasting 3-4 days and no use is made of antibiotics unless bacteria are present.

Lower Respiratory Tract Diseases.

Bronchiolitis

Bronchiolitis, a frequent disease in paediatric age, is characterised by an extensive inflammation of the airways accompanied by an intense production of mucus and necrosis of epithelial cells. It is primarily caused by a viral infection, particularly by RSV (respiratory syncytial virus), but also adenovirus, influenza and parainfluenza viruses, human metapneumovirus and rhinovirus, whereas the most frequently involved bacteria are of the genus *Clamidia*.

In paediatric age the principal clinical manifestations are tachypnea, breathlessness or crackles on auscultation, which generally follow an infection of the upper respiratory tract.

Treatment can entail hospitalisation if the saturation of oxygen is comprised between 92% and 94%, together with other clinical manifestations such as poor nutrition, dehydration and a history of dyspnea.

Cystic Fibrosis

This disease is caused by a mutation of the gene that codes for the protein CFTR, an anion channel expressed in epithelial cells throughout the body. Although it functions above all as a chloride ion channel, it is also capable of regulating the function of other membrane proteins, such as the epithelial sodium channel (ENaC), whose activity is inhibited. Among its many functions, CFTR also regulates the intracellular secretion of bicarbonate, which is reduced and determines a lowering of the epithelial pH with a consequent reduction in the protection against microbes and an increase in the viscoelasticity of mucus. The dysfunction of the CFTR channel in the lungs determines an excessive absorption of sodium and a reduced active secretion of chlorine, with a consequent reduction in the liquid layer on the surface of the mucosa. This leads to an anomalous mucus-ciliary clearance, with a retention of viscous mucus, which favours infections and inflammation and thus lung damage.

Various studies support the hypothesis that the lung damage is also caused by the vulnerability of the dehydrated mucosa. Based on this, it has been hypothesised that hypertonic saline solutions might be a new option for increasing the hydration of the mucosa and improving mucus-ciliary clearance.

Bronchiectasis

It is a pathology characterised by an irreversible dilation of a portion of the bronchial tree in the lungs. Bronchial dilation can be the result of a structural defect of the wall, exposure to an abnormal pressure, or damage to the cartilage or elastic tissue as a result of an inflammation. Bronchiectasis affects the bronchi and bronchioles, where a vicious circle of infection and inflammation can arise, also with the release of mediators. Common symptoms are coughing up mucus and chest pain.

The mucus contains an increased amount of elastase, TNF a, IL-8 and prostanoids. Bronchiectasis can manifest itself as a local obstructive process or a diffuse one involving part of both lobes, also accompanied by sinusitis or asthma. There are various causes; for example, above all in paediatric age, infections, including mycotic ones, which leave permanent damage, or else primary ciliary dyskinesias, in which there is a marked retention of the secretions followed by infections. Cystic fibrosis, as well as conditions of immunodeficiency, can be predisposing factors. It has further been observed that respiratory tract infections and bronchiectasis are present in patients with ulcerous colitis. Treatment entails the use of antimicrobials to combat the infections sustained both by bacteria and fungi. Furthermore, it is particularly useful to do lavages of the airways to increase the removal of secretions, making use of saline solutions and, as a general rule, keeping the patient well hydrated.

Other respiratory tract pathologies include asthma, chronic obstructive pulmonary disease (COPD) and other obstructive bronchial pathologies.

The pharmacological treatments available for the respiratory tract disorders listed above generally have scant effectiveness, are largely dependent on the individual response of the affected subjects and may have side effects, also major ones, such as skin rash and itching, headache, dizziness, sleep disorders (antibiotics), muscle cramps, tachycardia, trembling, anxiety and bronchial hyperreactivity ($\beta_2$-adrenergic agonists).

Other treatments, such as the administration of a hypertonic saline solution, besides having scant effectiveness, must be repeated a number of times and for long periods.

There is still a felt need to have a treatment making it possible to prevent or cure respiratory tract disorders without the disadvantages of the currently available therapies.

One aim of the present invention is to provide a treatment that makes it possible to prevent or cure respiratory tract disorders and which is effective, well tolerated and fundamentally devoid of side effects.

As a solution to said need, the present invention provides a composition for use in a treatment method according to the appended claims.

The present invention relates to a composition comprising or, alternatively, consisting of an effective amount of a mixture which comprises at least, or consists of:
 a) an extract of *Pelargonium sidoides;*
 b) an extract of *Adhatoda vasica*; and
 c) N-acetyl cysteine
for use in a method for the preventive or therapeutic treatment of at least one respiratory tract disorder in a subject, wherein said treatment method comprises the administration of said composition to the subject.

The subject matter of the present invention also relates to a pharmaceutical composition, dietary supplement or composition for a medical device comprising or, alternatively, consisting of an effective amount of a mixture which comprises at least, or consists of:
 a) an extract of *Pelargonium sidoides;*
 b) an extract of *Adhatoda vasica*; and
 c) N-acetyl cysteine
and at least one inert ingredient or excipient adapted for pharmaceutical, dietary or nutraceutical use.

The subject matter of the present description also relates to a method for the preventive or therapeutic treatment of at least one respiratory tract disorder in a subject, wherein said treatment method comprises the administration of the composition of the invention to said subject.

Finally, the subject matter of the present description also relates to the non-therapeutic use of the composition of the invention for the non-therapeutic, preventive or ameliorative treatment of at least one respiratory tract disorder in a subject, wherein said use comprises the administration of the composition of the invention to said subject.

Preferred embodiments of the present invention will emerge clearly from the detailed description that follows and are specified in the appended claims.

Within the scope of the present invention, the term "airways" indicates the upper or lower airways indistinctly, i.e. the composition of the invention can be active on an upper or lower respiratory tract disorder or on an upper and lower respiratory tract disorder.

Following extensive trials, the inventors have developed a composition comprising two natural extracts a) and b) and N-acetyl cysteine c), which has demonstrated high activity in the treatment and/or prevention of respiratory tract disorders. Without being limited by the theory, said high activity can be due to the synergistic action between components a), b) and c) as indicated above.

Within the scope of the present invention, "treatment method", or method for the treatment of a pathology or disorder, means therapy aimed at restoring the health conditions of a subject, maintaining the existing conditions and/or preventing the worsening of said health conditions.

Within the scope of the present invention, "prevention" of a pathology or disorder means therapy aimed at avoiding the onset of such a pathology or disorder in a subject, also, but not only, as a complication or effect of a pre-existing pathological condition or disorder.

Unless specified otherwise, within the scope of the present invention the percentages and amounts of a component in a mixture are intended to refer to the weight of that component relative to the total weight of the mixture.

Unless specified otherwise, within the scope of the present invention, in relation to numerical ranges of values for a certain characteristic, the indication "from X to Y" includes the extremes, that is, X and Y, in addition to all of the possible intermediate numerical values.

In the context of the present invention, the term "composition(s)" is intended to include a pharmaceutical composition, a composition for a dietary supplement, a composition for a food product or a composition for a medical device.

In one aspect, the present invention provides a composition comprising or, alternatively, consisting of an effective amount of a mixture which comprises at least, or consists of:
 a) an extract of *Pelargonium sidoides;*
 b) an extract of *Adhatoda vasica*; and
 c) N-acetyl cysteine
for use in a method for the preventive or therapeutic treatment of at least one respiratory tract disorder in a subject, wherein said treatment method comprises the administration of said composition to the subject.

Mucus hypersecretion is a condition characterising various respiratory tract pathologies such as asthma, cystic fibrosis and other obstructive bronchial pathologies. In healthy subjects, the production of mucus is not excessive and the latter is easily removed by the ciliary cells lining the wall of the respiratory tract. In the presence of some pathologies, mucus hypersecretion may occur or its removal by ciliary cells may be reduced as a result of infections, inflammation or irritation, so that it becomes necessary to use treatments making it possible to reduce these problems and thereby improve the respiratory capacity. There exist numerous classes of drugs capable of alleviating the symptoms of mucus hypersecretion, such as expectorants, mucolytics, mucoregulators and mucokinetics.

N-acetyl-L-cysteine (NAC or simply N-acetyl cysteine) is the acetylated form of the amino acid L-cysteine and is presently also used to limit the toxicity of paracetamol in the event of overdose and as a mucolytic agent.

The mechanism of action consists in reducing the disulphide bridges of the proteins present in mucus: this makes it possible to reduce its viscosity and facilitate its elimination. A further mechanism of action has been proposed, based on the anti-inflammatory and antioxidant activity of this molecule, which could enable a greater reduction of the symptoms of chronic obstructive pulmonary disease (COPD) with the use of NAC compared to other pharmacological treatments.

This was demonstrated by the HIACE study, during which it was observed that in patients affected by COPD there was an improvement in the forced expiratory flow, which rose from 25% to 75%, and a reduction in exacerbations (from 1.71 times a year to 0.96). Another series of studies likewise suggest the efficacy of using NAC to treat COPD: in this case it emerged that patients under treatment for six months with this molecule showed a significant increase in FEV1 (forced expiratory volume at the first second) and maximum expiratory flow, whilst another study showed an increase in FEV1 from 25% to 30% after a brief therapy of 4 weeks. The exacerbations of the pathology were reduced by 0.07 exacerbations/month and the days of malaise were reduced by 0.56 days/month, which enabled hospitalisations for COPD to be reduced by 30%. As previously mentioned, N-acetyl cysteine shows to be effective against COPD thanks not only to the mucolytic effect, but thanks also to the anti-inflammatory one. NAC is in fact capable of influencing various factors involved in the inflammatory process, thereby reducing the chemotactic capacity of the mucus of patients after 10 months of treatment and modulating the inflammatory response after 10 weeks of administration.

Furthermore, a meta-analysis demonstrated the benefits of prolonged use of N-acetyl cysteine for the treatment and prevention of chronic bronchitis, which has demonstrated to be capable of preventing acute exacerbations of this pathology. For these reasons, N-acetyl-L-cysteine has application in the treatment of various pathologies affecting the upper respiratory tract, such as pulmonary emphysema, bronchitis, amyloidosis and COPD. N-acetyl cysteine has demonstrated to be effective also in the treatment of cystic fibrosis. With regard to the treatment of upper and lower respiratory tract infections affecting children who do not present with chronic bronchopulmonary disorders, the use of N-acetyl cysteine and carbocysteine has brought about only slight improvements (reduction of coughing after 7 days), which have little clinical relevance.

N-acetyl cysteine is also effective in cases of idiopathic pulmonary fibrosis and numerous mechanisms of action in this pathology have been proposed.

It has in fact been demonstrated that NAC is capable of inhibiting the accumulation of collagen in cases of pulmonary fibrosis induced by bleomycin, increasing the amount of glutathione in the bronchoalveolar fluid of patients, and inhibiting various profibrotic mechanisms, such as increases in the levels of hydroxyproline, collagen, various cytokines, inflammatory cells, mucus secreting cells and mucin 5 subtypes A and C. Furthermore, it has demonstrated effectiveness in inhibiting the epithelial-mesenchymal transition in rat alveolar cells and reducing the expression of fibronectin, VEGF and α-SMA in human pulmonary fibroblasts and the concentration of cytokines produced by alveolar macrophages.

At present there are no clinical studies capable of demonstrating the greater efficacy of N-acetyl cysteine on its own in the treatment of pulmonary fibrosis, but it emerged from the "IFIGENIA" study that treatment with NAC, prednisone and azathioprine revealed to be more effective than the combination of prednisone+azathioprine (M. Demedts et al., "High-Dose Acetylcysteine in Idiopathic Pulmonary Fibrosis," *N. Engl. J. Med.*, vol. 353, no. 21, pp. 2229-2242, Nov. 2005).

Numerous studies demonstrate that the combined administration of NAC and hypertonic saline solution could lead to an improvement in respiratory activity in numerous pathologies, thanks to the mucolytic action of NAC and the expectorant effect of hypertonic saline solutions (DE 41 03 360 A1). It was judged that the best route of administration was aerosol inhalation, since in this manner N-acetyl cysteine is in able to interact directly with the mucoproteins lining the upper respiratory tract. Accordingly, there is a possibility of minimising such side effects as nausea, vomiting, drowsiness, headache, rash and fever, which have been found in various cases following oral administration of NAC.

*Pelargonium sidoides*

*Pelargonium sidoides* is one of the most important species of the genus *Pelargonium* long used in traditional medicine in South Africa.

The popular use of this type of plant was focused on respiratory infections and gastrointestinal problems; in particular, the interest in this plant species has increasingly grown because of its potential use as an antitubercular and as a remedy for earache, colds, tonsillitis, bronchitis, sinusitis and rhinopharyngitis (H. Kolodziej, O. Kayser, O. A. Radtke, A. F. Kiderlen, and E. Koch, "*Pharmacological profile of extracts of Pelargonium sidoides and their constituents*" *Phytomedicine*, vol. 10 Suppl 4, no. February, pp. 18-24, 2003).

From a phytochemical viewpoint, numerous studies have been aimed at identifying the main metabolites in plant extracts and the presence of an ample number of metabolites belonging to the classes of coumarins, flavonoids, proanthocyanidins, phenolic acids and phenylpropanoids has been detected. In particular, "umcalin" and other trimethoxy-coumarins are considered markers of the species *Pelargonium sidoides*, for distinguishing it, for example, from the species *Pelargonium reniforme*, in which these compounds should be absent.

The scientifically recognised effects of *P. sidoides* are antibacterial, antiviral and immunomodulatory effects attributed, respectively, to polyphenols (gallic acid) and a combination of phenolic compounds and compounds with a coumarinic structure.

With respect to antibacterial and antifungal activity, a 1997 study assessed the effect of the individual components (scopoletin, "umcalin", 5,6,7-trimethoxy-coumarin, (+)-catechin, gallic acid and esters thereof) against Gram-positive bacteria (*Staphylococcus aureus, Streptococcus pneumoniae, Streptococcus* 1451) and Gram-negative bacteria (*Escherichia coli, Klebsiella pneumoniae, Proteus mirabilis, Pseudomonas aeruginosa, Haemophilus influenzae*). All of the components except catechin showed antibacterial activity with an MIC comprised between 200 μg/mL and 1000 μg/mL.

The antibacterial activity has also been indirectly evaluated by assessing the ability of an extract of *Pelargonium sidoides* to inhibit bacterial adhesion (*streptococcus*) to human epithelial cells. Other in vitro studies have shown the plant extract to be capable of increasing phagocytosis, the oxidative response and cell death.

Other studies have confirmed the significant immunomodulatory power of extracts of *Pelargonium*, which are capable of stimulating not only macrophage activity, but also the release of a series of cytokines that are fundamental in the immune response, e.g. TNF-α, iNOS, IL-1, IL-10, IL-12, IL-18 and interferon-α, γ. This immunomodulatory action is of particular importance, also considering that the majority of infections affecting the upper respiratory tract are due to viruses.

Another documented activity of the plant extract is the ability to stimulate the mucociliary system: an ability of the plant extract (1, 30, 100 μg/mL) to increase mucociliary clearance in cultures of human nasal epithelial cells was observed in two studies.

It has emerged from an ample number of clinical trials that the extract of *Pelargonium sidoides* has good effectiveness and at the same time a good safety of use (side effects are mainly mild and transitory).

The extract of *Pelargonium sidoides* a) used in the composition of the present invention is advantageously an extract of leaves, fruits, seeds, cortex, branches or roots or, alternatively, an extract obtained from two or more of said rparts of the plant. Said extract of *Pelargonium sidoides* a) used in the composition of the present invention is preferably a dry hydroalcoholic extract obtained according to standard procedures known to the person skilled in the art and/or reported in the literature.

*Adhatoda vasica*

*Adhatoda vasica*, also known as *Justicia adhatoda* L., is a medicinal plant of the family Acanthaceae, native to Asia.

The plant grows spontaneously and abundantly throughout Nepal, India and in the Pothohar region of Pakistan, particularly in the Pharwala area.

Flowering takes place between November and April in flatlands, July and October in hilly areas.

Phytochemical studies on this plant have revealed the presence of alkaloids, phytosterols, polyphenols and glycosides as the principal chemical compounds. The main constituents are quinazoline alkaloids, with vasicine being the most representative compound. In addition to vasicine, the leaves and roots of this plant contain other alkaloids, such as I-vasicinone, deoxyvasicine, maiontone, vasicinolone and vasicinol.

The leaves are rich in vitamin C and carotenoids. The chemical compounds present in the leaves and roots of the plant include essential oils, fats, resins, sugars, amino acids and vitamins.

*Adhatoda* has been used in traditional medicine to treat respiratory disorders. Vasicine and vasicinone are known as therapeutic agents for the treatment of respiratory tract disorders. The extracts of the leaves and roots of *Adhatoda* are used for the treatment of bronchitis and other pathologies of the bronchioles and lungs, such as coughing and colds. The bronchodilating activity of vasicine has been demonstrated both in vitro and in vivo. Vasicinone, the principal metabolite of vasicine, has shown bronchodilating activity in vitro, but bronchoconstricting activity in vivo. The antitussive activity has been demonstrated in in vivo studies on guinea pigs and rabbits. Recent studies on vasicine have demonstrated its bronchodilating activity both in vitro and in vivo.

Another pharmacological property that is very useful for the purpose of treating respiratory pathologies may be antibacterial activity. In vitro studies have demonstrated the strong activity of the alkaloids of *Adhatoda* against the bacteria *Pseudomonas aeruginosa, Streptococcus faecalis, Staphylococcus aureus* and *Escherichia coli*.

Vasicine and vasicinone have also demonstrated to have anti-allergic activity. In an in vivo study, an extract containing vasicinol and vasicine at a dose of 5 mg demonstrated to inhibit the allergic response induced by ovalbumin by 37%.

The extract of *Adhatoda vasica* b) used in the composition of the present invention is advantageously an extract of leaves, roots or flowers or, alternatively, an extract obtained from roots and/or leaves; it is preferably an extract of leaves. Said extract of *Adhatoda vasica* b) preferably used in the composition of the present invention is a dry extract obtained according to standard procedures known to the person skilled in the art and/or reported in the literature.

Extracts a) and b) and N-acetyl cysteine c) have demonstrated a synergistic action, i.e. more than additive, in the prevention and treatment of lower and/or upper respiratory tract pathologies. For example, the composition according to the present invention makes it possible to obtain the therapeutic effects obtainable with high doses of N-Acetyl cysteine despite a reduction in the amount of NAC actually administered, thus significantly decreasing the possibility of side effects.

The present invention makes it possible to obtain, simultaneously:

Mucolytic effect;

Antimicrobial effect.

N-acetyl cysteine has the ability to reduce the disulphide bridges of mucin. In this manner, NAC reduces the viscosity of mucus. *Adhatoda vasica* also shows mucolytic activity which, combined with the bronchodilating activity, is capable of contributing further to the wellbeing of the respiratory tract.

Extract of *Pelargonium sidoides* is endowed with antimicrobial activity against many microorganisms, including bacteria and viruses which can be the cause of pathologies affecting the respiratory tract. Another interesting activity of *Pelargonium sidoides* is its immunomodulatory activity, which should contribute further to preventing infections that are a cause of respiratory tract pathologies.

The synergistic action takes place between N-Acetylcysteine, extract of *Pelargonium sidoides* and extract of *Adhatoda vasica*, particularly, but not exclusively, when N-acetyl cysteine is present in an amount of 100 mg to 1500 mg, preferably 200 mg to 1200 mg; the extract of *Pelargonium sidoides* is present in an amount of 1 mg to 500 mg, preferably 1 mg to 100 mg, more preferably 10 mg to 60 mg; and the extract of *Adhatoda vasica* is present in an amount of 50 mg to 2000 mg, preferably 75 mg to 800 mg, more preferably 100 mg to 600 mg.

The composition according to the present invention is preferably for use in a treatment method of at least one respiratory tract disorder from among rhinitis, sinusitis, pharyngitis, epiglottitis, laryngitis, bronchiolitis, cystic fibrosis, chronic obstructive pulmonary disease and bronchiectasis.

The composition according to the present invention is preferably for use in the aforesaid treatment method comprising administration via the oral, nasal or inhalation route.

The composition according to the present invention is preferably in the form of liquid composition for oral use and/or a powder that is soluble or dispersible in a liquid.

In the composition for use according to the present invention, said mixture preferably comprises an amount of extract of *Pelargonium sidoides* a) of 1 to 100 mg, more preferably 10 to 60 mg.

In the composition for use according to the present invention, said mixture preferably comprises an amount of extract of *Adhatoda vasica* a) of 50 to 100 mg, more preferably 75 to 800 mg, even more preferably 100 to 500 mg.

In the composition for use according to the present invention, said mixture preferably comprises an amount of N-acetyl cysteine ranging from 50 to 2000 mg, preferably 200 to 1200 mg.

In the composition for use according to the present invention, said mixture preferably comprises an extract of *Pelargonium sidoides* a) and an extract of *Adhatoda vasica* b) in an a):b) weight ratio of 1:2 to 1:50, preferably 1:5 to 1:30 or 1:9 to 1:20.

In the composition for use according to the present invention, said mixture preferably comprises an amount of N-acetyl cysteine c) in a weight ratio with the total weight of the extract of *Pelargonium sidoides* a) and extract of *Adhatoda vasica* b), c): [a)+b)] ranging from 50:1 to 1:10, preferably 30:1 to 1:3 or 10:1. to 6:1.

The composition according to the present invention is preferably for the therapeutic or preventive treatment of at least one respiratory tract disorder from among rhinitis, sinusitis, pharyngitis, epiglottitis, laryngitis, bronchiolitis, cystic fibrosis and bronchiectasis.

The composition according to the present invention can be for use in human subjects, also, but not only, of paediatric age, or for veterinary use, for example, but without limitation, in pets such as dogs or cats, or in other mammals. The composition according to the present invention is preferably for use in humans.

In one embodiment, the administration of the composition to the subject takes place orally, for example in the form of a tablet, pill, also coated, capsule, mouth-dissolving powder, solution, suspension, also obtained by dissolution or suspension of a powder in a liquid such as an aqueous medium, syrup, food containing extracts a) and b) and N-acetyl cysteine c) or in any other form known to the person skilled in the art.

In one embodiment, the administration of the composition to the subject takes place by inhalation, for example in the form of an aerosol, nebulised suspension or nasal or oral spray.

It remains understood that the administration of extracts a) and b) and N-acetyl cysteine c) according to the invention can take place simultaneously, for example in a single formulation, or in rapid sequence, for example by means of two or more formulations taken by the subject in any order, in a sequence closely spaced over time (e.g. within 1 to 10 minutes) in two or more distinct compositions.

The composition for use according to the present invention may comprise, in addition to extracts a) and b) and N-acetyl cysteine c), at least one inert ingredient, such as at least one excipient among those commonly used and known to the person skilled in the art.

"Inert ingredient" means any substance, or combination of substances, auxiliary to the production of a pharmaceutical, dietary or nutraceutical form, which is to be found in the finished product and is not the active ingredient, although it can modify the stability, release or other characteristics thereof.

Non-limiting examples of such ingredients, as known to the person skilled in the art of formulations in the pharmaceutical, nutraceutical or food sectors, are diluent, absorbent, adsorbent, lubricant, glidant, colouring, surfactant, antioxidant, sweetening, flavouring, binding, disintegrating, plasticising, viscosity enhancing, emulsifying, humectant, wetting, preservative and chelating excipients and the like.

In one embodiment, the composition for use according to the present invention comprises, in addition to extracts a) and b) and N-acetyl cysteine c), at least one further active ingredient of natural or synthetic origin. Non-limiting examples of said active ingredients are thiamine, riboflavin, pantothenic acid, niacin, biotin and ascorbic acid.

In a preferred embodiment, the composition for use according to the present invention contains, in addition to extracts a) and b) and N-acetyl cysteine c), at least one other active ingredient selected from among extracts of *Hedera helix* L., hederagenin, *Glycyrrhiza glabra* L., glycyrrhizic acid, 18β-glycirrhetic acid, *Papaver rhoeas* L., *Grindelia humilis* Nutt., *Eucalyptus globulus* Labill. and 1,8-cineole.

In one aspect, the present invention provides a pharmaceutical composition, dietary supplement or composition for a medical device comprising or, alternatively, consisting of an effective amount of a mixture which comprises at least, or consists of:

a) an extract of *Pelargonium sidoides*;
b) an extract of *Adhatoda vasica*; and
c) N-acetyl cysteine and at least one inert ingredient or excipient adapted for pharmaceutical, dietary or nutraceutical use.

In the context of the present invention, the term "medical device" is used with the meaning according to Italian Legislative Decree no. 46 of 24 Feb. 1997, and Directive 93/42/EEC of 14 Jun. 1993, i.e. it indicates a substance or another product, whether used alone or in combination, intended by the manufacturer to be used for human beings for the purpose of diagnosis, prevention, monitoring, treatment or alleviation of a disease, and which does not achieve its principal intended action in or on the human body for which it is intended by pharmacological, immunological or metabolic means, but which may be assisted in its function by such means.

The pharmaceutical composition, dietary supplement or composition for a medical device of the present invention can be solid, liquid or semisolid, for example a suspension or gel, and it can be in any form known to the person skilled in the art of food, pharmaceutical or nutraceutical formulations; by way of non-limiting example, in the form of a capsule, tablet, or powder that is at least partially dissolvable in the mouth or water soluble, granules, pellets or microparticles optionally contained in a sachet or in a capsule or mini-tablet, a liquid or semisolid preparation, gel, suspension, solution, two-phase liquid system and equivalent forms.

Non-limiting examples of compositions according to the present invention are represented by:

Example 1

| Active ingredient | Daily dose |
| --- | --- |
| N-Acetylcysteine | 600 mg |
| *Adhatoda vasica*, d.e. | 300 mg |
| *Pelargonium sidoides* | 30 mg | d.e.: dry extract
Pharmaceutical form: Sachets.

Example 2

| Active ingredient | Daily dose |
| --- | --- |
| N-Acetylcysteine | 1,200 mg |
| *Adhatoda vasica*, d.e. | 600 mg |
| *Pelargonium sidoides* | 60 mg |

Pharmaceutical form: Sachets.

Example 3

| Active ingredient | Daily dose |
| --- | --- |
| N-Acetylcysteine | 600 mg |
| *Adhatoda vasica*, d.e. | 300 mg |
| *Pelargonium sidoides* | 30 mg |

Pharmaceutical form: Bottle of oral liquid.

Example 4

| Active ingredient | Daily dose |
| --- | --- |
| N-Acetylcysteine | 200 mg |
| *Adhatoda vasica*, d.e. | 100 mg |
| *Pelargonium sidoides* | 20 mg |

Pharmaceutical form: Bottle of oral liquid.

Example 5

| Active ingredient | Daily dose |
| --- | --- |
| N-Acetylcysteine | 600 mg |
| *Adhatoda vasica*, d.e. | 100 mg |
| *Pelargonium sidoides* | 20 mg |

Pharmaceutical form: Sachets.

Example 6

| Active ingredient | Daily dose |
| --- | --- |
| *Adhatoda vasica*, d.e. | 300 mg |
| N-Acetylcysteine | 100 mg |
| *Pelargonium sidoides* | 10 mg |

Pharmaceutical form: Bottle of oral liquid.

The following experimental part provides examples of practical embodiments of the invention, without limiting the scope thereof.

EXPERIMENTAL PART

1) Material

The pharmaceutical forms illustrated below are prepared according to standard techniques known to the person skilled in the art for the preparation of solid and liquid compositions for pharmaceutical, nutraceutical and/or dietary use in humans.

Example 1

| Active ingredient | Daily dose |
| --- | --- |
| N-Acetylcysteine | 600 mg |
| *Adhatoda vasica*, d.e. | 300 mg |
| *Pelargonium sidoides* | 30 mg |

Pharmaceutical form: Sachets.

Example 2

| Active ingredient | Daily dose |
| --- | --- |
| N-Acetylcysteine | 1,200 mg |
| *Adhatoda vasica*, d.e. | 600 mg |
| *Pelargonium sidoides* | 60 mg |

Pharmaceutical form: Sachets.

Example 3

| Active ingredient | Daily dose |
| --- | --- |
| N-Acetylcysteine | 600 mg |
| *Adhatoda vasica*, d.e. | 300 mg |
| *Pelargonium sidoides* | 30 mg |

Pharmaceutical form: Bottle of oral liquid.

Example 4

| Active ingredient | Daily dose |
| --- | --- |
| N-Acetylcysteine | 200 mg |
| *Adhatoda vasica*, d.e. | 100 mg |
| *Pelargonium sidoides* | 20 mg |

Pharmaceutical form: Bottle of oral liquid.

Example 5

| Active ingredient | Daily dose |
| --- | --- |
| N-Acetylcysteine | 600 mg |
| *Adhatoda vasica*, d.e. | 100 mg |
| *Pelargonium sidoides* | 20 mg |

Pharmaceutical form: Sachets.

Example 6

| Active ingredient | Daily dose |
| --- | --- |
| *Adhatoda vasica*, d.e. | 300 mg |
| N-Acetylcysteine | 100 mg |
| *Pelargonium sidoides* | 10 mg |

Pharmaceutical form: Bottle of oral liquid.

2) Methods

The effectiveness of the composition of the present invention in a method for the treatment of at least one respiratory tract disorder and/or the synergistic action of components a), b) and c) of the composition itself was assessed using in vitro and in vivo methods known to the person skilled in the art, as described below.

The anti-inflammatory activity of the individual components compared to the combination thereof (composition of the present invention) and compared to the control was assessed in vitro. Specifically, mouse monocyte/macrophage J774 cell lines were selected and grown in DMEM (Dulbecco's Modification of Eagle Medium) with the addition of glutamine, Hepes, penicillin, foetal bovine serum and sodium pyruvate. The cells were plated and kept in an incubator at a controlled temperature and atmosphere. Cell viability was assessed by means of the MTT assay (3-(4,5-dimethylthiazol-2-yl)-2,5-diphenyltetrazolium bromide) and the growth thereof was subsequently stimulated. At this point, specific methods were used to measure the concentration of nitrites, levels of TNF-α and IL-1β as parameters for assessing anti-inflammatory activity.

The antimicrobial activity of the composition of the present invention was assessed in vitro. Suitable assays include broth dilution (with the calculation of the MIC, or minimum inhibitory concentration, and MBC, or minimum bactericidal concentration) and diffusion in agar (where a standardised concentration of the sample is applied in a broth culture of bacteria and the diffusion of the sample within the medium is calculated). The antimicrobial activity was assessed in the main bacterial strains belonging to the Gram-positive and/or Gram-negative categories and/or other microbial species.

The antioxidant activity of the composition of the present invention, of particular interest for alleviating respiratory tract disorders, was assessed in vitro. Suitable in vitro assays include, for example: DPPH assay (nitrogen radical 2,2-diphenyl-1-picrylhydrazyl), radical scavenging activity on nitric oxide or on the peroxynitrile radical, TEAC assay (total radical-trapping antioxidant parameter), FRAP (ferric reducing-antioxidant power), HORAC (hydroxyl radical averting capacity), ORAC (oxygen radical absorbance capacity) and the like.

The expectorant activity of the composition of the present invention was assessed in vivo in CD1® mice. Specifically, the animals were treated with different formulations (e.g. individual active components, active components in association, vehicle, control) administered orally. Several minutes after treatment, the animals received an intraperitoneal injection of phenol red; the mice were subsequently anaesthetised, the upper front part of the neck was shaved and the trachea was exposed. The mice then underwent a tracheobronchial lavage with saline solution and the lavage fluid was subsequently recovered and centrifuged. As a parameter for evaluating the expectorant activity, the post-lavage concentration of red phenol was measured by spectrophotometry.

The anti-tussive effect of the composition of the present invention was tested in an in vivo model of guinea pigs with coughing provoked by inhalation of capsaicin. The anaesthetised animals were exposed to a nebulised aqueous solution of capsaicin and during exposure they were observed constantly in order to assess the number of coughing episodes. The majority of coughing episodes occurred within 10 minutes, which was the time then established as the duration of exposure. This model proposes pre-treating the guinea pigs with the active components of the present invention (a), b) and c)) orally administered, individually or in a mixture (composition according to the invention), 30 minutes before inhalation with capsaicin, to demonstrate how the number of coughing episodes is considerably reduced by the synergistic action of the components compared to the same ones tested individually.

The invention claimed is:

1. A composition comprising a synergistically-effective amount of a mixture of:
    a) an extract of *Pelargonium sidoides*;
    b) an extract of *Adhatoda vasica*; and
    c) N-acetyl cysteine.

2. The composition according to the claim 1, wherein said composition is formulated for inhalation.

3. The composition according to the claim 1, wherein the composition is formulated as an aerosolizable powder or liquid.

4. The composition according to claim 1, wherein said mixture comprises an amount of extract of *Pelargonium sidoides* a) ranging from 1 mg to 100 mg; an amount of extract of *Adhatoda vasica* b) ranging from 50 mg to 1000 mg; and/or an amount of N-acetyl cysteine ranging from 50 mg to 2000 mg.

5. The composition according to claim 1, wherein said mixture comprises an extract of *Pelargonium sidoides* a) and an extract of *Adhatoda vasica* b) in a weight ratio in the range of 1:2 to 1:50.

6. The composition according to claim 1, wherein said mixture comprises an amount of N-acetyl cysteine in a weight ratio with the total weight of the extract of *Pelargonium sidoides* a) and extract of *Adhatoda vasica* b) ranging from 50:1 to 1:10.

7. A pharmaceutical composition, dietary supplement or composition for a medical device comprising a synergistically-effective amount of a mixture of:
    a) an extract of *Pelargonium sidoides*;
    b) an extract of *Adhatoda vasica*; and
    c) N-acetyl cysteine
and at least one inert ingredient or excipient adapted for pharmaceutical, dietary or nutraceutical use.

8. The composition of claim 1, wherein the composition is formulated for oral administration.

9. The composition of claim 8, wherein the composition is formulated as a capsule, tablet, powder or liquid.

* * * * *